United States Patent [19]

Burke et al.

[11] Patent Number: 4,595,006
[45] Date of Patent: Jun. 17, 1986

[54] APPARATUS FOR CEMENTED IMPLANTATION OF PROSTHESES

[76] Inventors: Dennis W. Burke, 24 Marine Rd., South Boston, Mass. 02127; William H. Harris, 665 Concord Ave., Belmont, Mass. 02178

[21] Appl. No.: 408,468

[22] Filed: Aug. 16, 1982

[51] Int. Cl.$^4$ .............................................. A61F 1/00
[52] U.S. Cl. ................................. 128/303 R; 623/16; 128/92 E
[58] Field of Search ............ 222/387, 389, 525, 386.5, 222/499; 604/88, 140, 150, 152; 128/92 C, 92 E, 92 R, 92 G, 303 R; 3/1, 1.9, 1.91

[56] References Cited
U.S. PATENT DOCUMENTS

| | | | |
|---|---|---|---|
| 1,718,597 | 6/1929 | Smith | 604/88 |
| 1,958,429 | 5/1934 | Hartog | 222/499 |
| 3,206,073 | 9/1965 | Scislowicz | 222/52 S |
| 3,486,539 | 12/1969 | Jacuzzi | 222/386.5 |
| 3,785,379 | 1/1974 | Cohen | 604/88 |
| 3,983,947 | 10/1976 | Wills et al. | 222/389 |
| 4,375,864 | 3/1983 | Savage | 222/499 |
| 4,399,814 | 8/1983 | Pratt, Jr. et al. | 128/92 E |
| 4,405,249 | 9/1983 | Scales | 128/92 G |
| 4,424,057 | 1/1984 | House | 604/88 |

Primary Examiner—Richard J. Apley
Assistant Examiner—David Isabella
Attorney, Agent, or Firm—Wolf, Greenfield & Sacks

[57] ABSTRACT

Apparatus and method for polymerizing cement under pressurized conditions and for applying the cement under pressure at the appropriate time to a human bone cavity for implantation of a prosthesis, including a stemmed femoral component and an acetabular component. This apparatus alters the physical conditions under which bone cement cures, causing a decrease in cement porosity and thus increasing the resultant cement strength. The apparatus includes a pneumatically actuated gun having a piston for applying pressure to the cement, and applying cement to the bone, a pressurizable housing securable to the gun for containing the cement, and a nozzle having a valve which allows the cement to remain pressurized until application thereof through the nozzle. In one embodiment, one component of a two component polymerizable cement is provided in a sealed bladder secured to the nozzle while the other component is injected into the bladder and mixed with the first component when the cement is ready for use. A vent may be provided in the piston of the pneumatic gun to allow air to escape through the piston to prevent the injection of air into the cement. A sealing gasket may be provided on the end of the nozzle for placement over the open end of the bone cavity so that cement can be applied thereto under pressure.

12 Claims, 10 Drawing Figures

APPARATUS FOR CEMENTED IMPLANTATION OF PROSTHESES

FIELD OF THE INVENTION

This invention relates generally to human prostheses and more particularly to apparatus and a method for injection of cement into a human bone cavity for implantation of a prosthesis, particularly a stemmed femoral component and an acetabular component.

BACKGROUND OF THE INVENTION

Load carrying skeletal members such as the human hip are frequently rendered non-functional because of arthritis, fracture, damage, disease, resections for malignancy or disease, or because of pain or malformation. Such members are commonly repaired by total joint replacement with artifical components, and one type of bone replacement that has been particularly successful over the past 22 years is that of the human hip. Such hip prostheses typically include a metal femoral portion or component which is implanted in the femur and a plastic acetabular component which is secured to the pelvis. The femoral component generally is formed in one piece and includes a stem, a collar, a neck and a head. The stem is adapted to be inserted into the medullary canal of a femur bone while the collar is adapted to rest on the cortical bone in the region of the femoral neck. The head is disposed on the end of the neck and is adapted to rotate within the acetabular component. Cement is most commonly used for implanting the stem in the femur, and examples of femoral components constructed to be cemented into the femur are illustrated in U.S. Pat. Nos. 3,744,061; 4,012,796; 4,146,936; 4,156,943; 3,808,606; 3,102,536; and 4,080,666.

Although many of the hip replacement prostheses described in the aforementioned patents have been used successfully, one significant complication which has developed with almost every known cemented replacement is the high rate of loosening thereof. Various reports of long term results of cemented total hip replacements with a minimum followup of 10 years show that the loosening rate on the femoral side is in the neighborhood of 30 to 50 percent. One reason for the reported high rate of loosening in cemented implants is the weakening or loss of strength of the cement bond resulting from use, which constitutes one primary weakness in the implant. If the cement strength, or the life of the cement bond between the implant and the femur could be increased, the life span of the implant would be significantly increased.

A methylmethacrylate cement is commonly used for cementing such stemmed components into the femur and for cementing acetabular components into the acetabulum. This cement typically consists of a powdered polymer and a liquid monomer which must be mixed together prior to use for polymerization to occur. This mixing is commonly done in a open bowl by hand and produces a gas which is partially released into the atmosphere and which remains partially within the polymerized cement to form bubbles therein. Also, air is drawn into the cement by the mixing process to form pores or bubbles. These bubbles produce a hardened cement having a high porosity.

In addition, this cement is typically injected into the bone cavity using a hand held and operated caulking gun, or syringe after it has been hand mixed in a separate container and hand poured into the gun. This whole process is very awkward because of the large number and variety of implements required and it can be very time consuming.

SUMMARY OF THE INVENTION

This invention relates generally to an efficient, automated apparatus for delivering cement to a bone cavity for implantation of a prosthetic device in the bone. The present invention overcomes many of the shortcomings of prior art implantation apparatus and techniques by providing means for pressurizing bone cement during its early stages of polymerization prior to insertion into the bone cavity. This pressurization reduces cement porosity thus increasing its strength. The apparatus of this invention includes a pneumatically actuated cylinder, a pressurizable housing which is removably secured to the cylinder and which is adapted to contain a polymerizable cement, a piston driven by the cylinder for pressurizing the housing and any cement therein and a nozzle extending from the housing for delivery of the cement to a bone cavity. Typically, the housing and nozzle are disposable so that only one housing and nozzle is used for each application. The nozzle is provided with a long snout which can be inserted into a bone canal and a valve which is on an end of the nozzle adjacent the housing and which is forced into a normally closed position during pressurization of the housing.

In the method of this invention, the cement is placed into the housing while it is in the process of polymerization and the piston is advanced to apply pressure on the cement. When the cement is ready to be applied, the valve is snapped open by depression of the nozzle toward the cylinder and the piston is advanced to urge the cement through the nozzle.

In another embodiment, the nozzle may be provided separately of the housing and with a bladder which is secured to the valved end and which contains a powdered, pre-polymerized cement sealed in a high vacuum. The bladder includes a needle valve through which the monomer may be injected in liquid form. The monomer and pre-polymerized cement powder are mixed within the bladder in a sealed environment to prevent possible contamination and the introduction of air bubbles within the cement during mixing. After mixing, this nozzle is secured to the housing with the bladder placed within the housing, and the housing and nozzle are secured to the cylinder. The piston is then advanced to pressurize the housing and the cement within the bladder, and thereafter to eject the cement through the nozzle.

Another feature of the invention includes a filter which may be provided in the piston and a vent which may be provided in the piston rod and lower housing to allow air to pass therethrough and escape from the housing during pressurization and application of the cement, so that no air is injected into the bone canal with the cement.

A further aspect of the invention includes a special high pressure gasket which is secured to the end of the nozzle during application of the cement to the bone cavity. This gasket is manually pressed against the opening of the bone cavity to create a seal. In this manner, cement can be forced into the bone cavity under pressure so that it invades all of the crevises and interstices of the interior of the cavity to provide a better bond between the cement and the bone, and to insure the integrity of the bone-cement interface.

The apparatus and method of this invention permits preparation of a standard polymer cement in a closed, high pressure environment prior to application to the bone cavity to inhibit the formation of bubbles and injection of air during the mixing process and during the application of cement to provide a low porosity, strong cement bond. In addition, the apparatus of this invention permits the application of the cement to a bone cavity for implantation of a prosthesis in a convenient, automated and accurate manner by providing for mixing, pressurization and application all in one, pneumatically actuated tool.

DESCRIPTION OF THE DRAWING

The objects, advantages and features of this invention will be more clearly appreciated from the following detailed description taken in conjunction with the accompanying drawing in which.

DETAILED DESCRIPTION OF THE PREFERRED EMBODIMENT

It has been found that one cause of the high observed loosening rate of total hip replacements is the weakness of the cement bond between the femoral component and the femur or between the acetabular component and the acetabulum. This weakness is due in part to the high porosity often observed in such cement since the cement strength is related to its porosity. Experimentation has shown that this cement porosity can be significantly reduced and thus the cement strength increased if the cement is pressurized during polymerization and during application to a bone cavity. The present invention permits the cement to be pressurized to increase its strength during at least a portion of the polymerization process and also while the cement is being applied to a bone cavity. Bone cavities for which this invention is particularly suited include the acetabulum, the femoral bone canal and any other bone cavity into which a prosthetic device is to be implanted.

Figure 1:
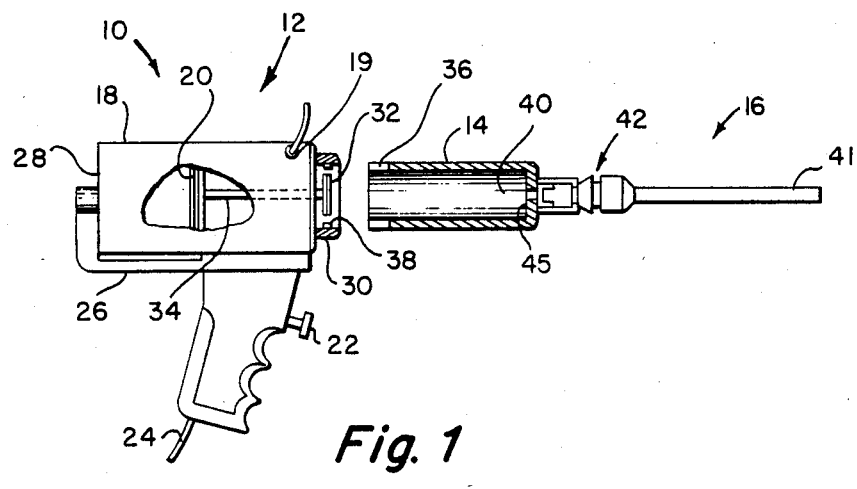
FIG. 1. is a pictorial representation of the apparatus of this invention in a partially disassembled condition.

With reference now to the drawing and more particularly to FIG. 1 thereof, apparatus 10 of this invention includes a pneumatically operated cylinder or gun 12, a pressurizable housing 14 adapted to be secured to one end of gun 12 and a nozzle 16 extending from housing 14.

Gun 12 typically includes a cylinder 18 and a piston 20 slidable therein in response to pneumatic pressure, and a trigger valve 22. Valve 22 selectively couples cylinder 18 to a source of pressurized gas upon depression thereof. Lines 24 connect valve 22 with a source of pressurized gas, while line 26 couples valve 22 with opening 28 in the rear end of cylinder 18. The front end of cylinder 18 is coupled to an exhaust by port 19 to allow piston 20 to move forwardly unimpeded when gas flows into cylinder 18 through opening 28 and to remove the gases within cylinder 18 from the operating room to prevent contamination of the air therein. The rear end of cylinder 18 is vented through opening 28 upon deactuation of trigger valve 22. Disposed on a forward end of gun 12 is a coupling 30 for providing a connection between housing 14 and gun 12. Also disposed on the forward end of gun 12 is a piston 32 which is adapted to ride within housing 14. Piston 32 is driven by piston 20 and is coupled thereto by rod 34.

Figure 2:
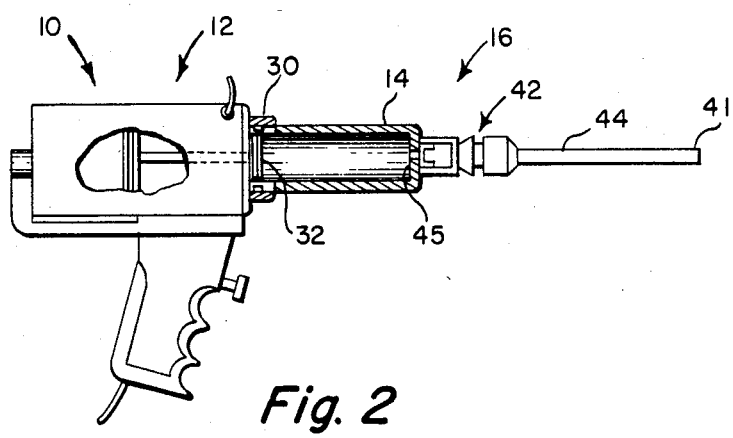
FIG. 2. is a pictorial representation of the apparatus of this invention and in an assembled condition.
Figure 3:
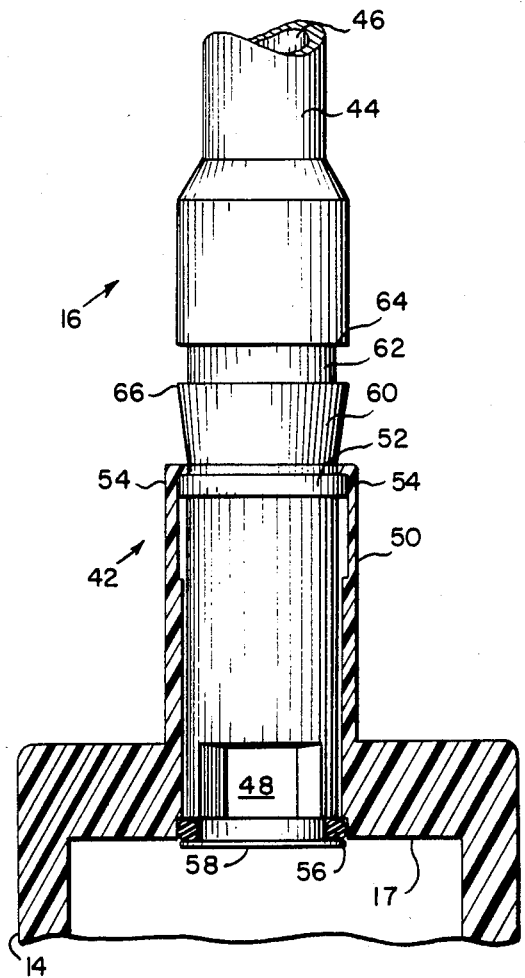
FIG. 3. is a partial cross-sectional view of the nozzle valve of this invention in a closed position.

Housing 14 is provided independently of gun 12 and may be disposable. Housing 14 typically is a hollow cylinder having means disposed on one axial end thereof adapted to cooperate with coupling 30 to secure housing 14 to gun 12. Typically, L-shaped notches 36 are provided, and coupling 30 includes projections 38 which register with notches 36. Projections 38 are forced into notches 36 by axially moving housing 14 toward gun 12 and by rotating housing 14 about its axis with respect to gun 12. Disposed at the other end of housing 14 is nozzle 16 which may be formed integrally with housing 14, as shown in FIGS. 2–4.

Nozzle 16 will be described with particular reference to FIGS. 1, 3 and 4. Nozzle 16 is typically formed of a plastic material and may be disposable, and it is integral with circular end wall 17 of housing 14. Nozzle 16 includes a valve 42 and an elongated generally cylindrical portion 44 or snout having a channel 46 formed therethrough for ejection of cement through distal end 41. Valve 42 provides fluid communication between the interior of housing 14 and channel 46. Valve 42 includes cylindrical housing 50 which surrounds portion 44 and is in sliding relationship therewith. Cap 58 covers the end of portion 44 disposed within housing 14, and ports 48 are formed on lateral walls of portion 44 adjacent cap 58. Valve 42 is shown in its normally closed position in FIG. 3 in which the pressure within housing 14 against cap 58 drives portion 44 outwardly away from housing 14. Laterally projecting ring 52 on portion 44 is driven against overlaping shoulders 54 of cylindrical housing 50 to prevent portion 44 from being forced out of housing 50. Flange 60 flares radially outwardly moving away from ring 52 toward distal end 41 and flange 60 biases valve 42 into its normally closed position to prevent it from being inadvertently opened. In this normally closed position, ports 48 reside within housing 50 and do not communicate with the interior of housing 14 and entry of cement into ports 48 is prevented by O-ring 56 which seals the space between the interior walls of housing 50 and the exterior walls of portion 44, and which rests on shoulders 49 . Cap 58 is roughly flush with the inner surface of circular end wall 17.

Figure 4:
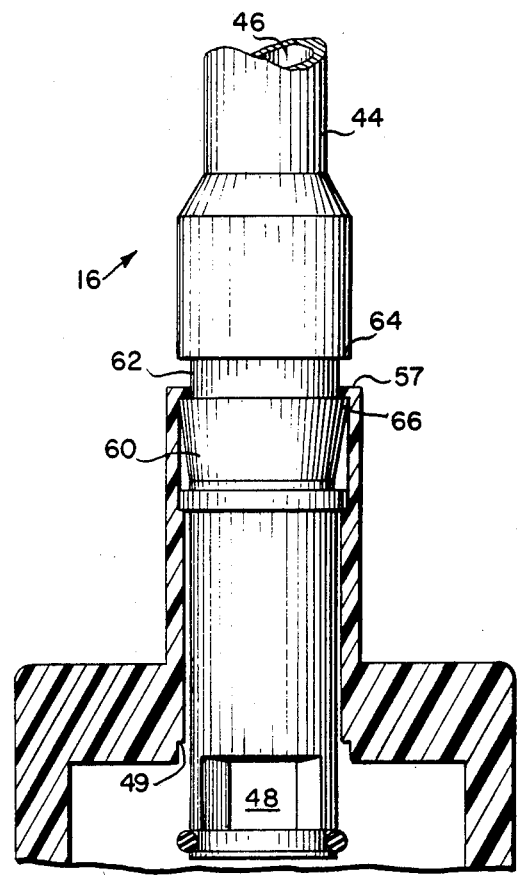
FIG. 4. is a partial cross-sectional view of the nozzle valve of this invention in an open position.

Valve 42 is shown in its open position in FIG. 4. Valve 42 may be opened manually by pushing inwardly on portion 44 with a predetermined pressure to force it toward housing 14, thus pushing ports 48 past end wall 17 and into the interior of housing 14 to allow communication between the interior of housing 14 and openings 48. Valve 42 is locked into the open position by flange 60. Flange 60 forces shoulders 54 radially outwardly as portion 44 is driven downwardly towards housing 14 until shoulders 54 pass indentation 62 formed on the outer surface of portion 44. At this point, portion 44 is prevented from being pushed inwardly farther into housing 14 by shoulders 64 of indentation 62, while portion 44 is also prevented from being forced outwardly away from housing 14 by pressure within housing 14 by shoulders 66, thus capturing shoulders 54 within indentation 62 and preventing reclosing of valve 42.

Figure 8:
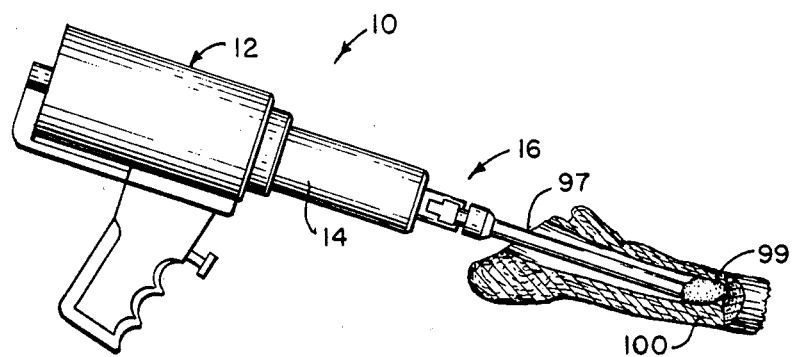
FIG. 8. is a pictorial representation of the use of the apparatus of this invention with a bone canal.
Figure 10:
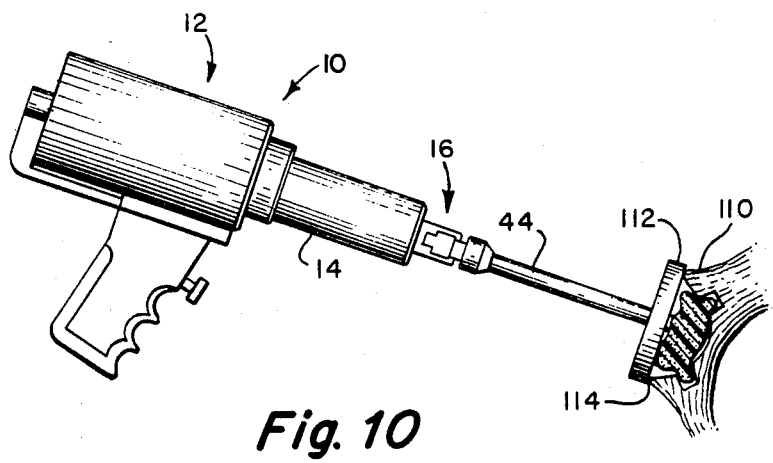
FIG. 10. is a pictorial representation of the use of the apparatus of this invention with an acetabular cavity.

The method and operation of the apparatus of FIGS. 1-4 will now be described. The monomer and pre-polymerized cement are mixed outside the apparatus, typically in an open bowl, to begin polymerization. The cement is then loaded into housing 14 while in a liquid or dough-like state. Housing 14 is then latched to gun 12 by projections 38 and notches 36 to provide a sealed environment within housing 14. Trigger valve 22 is actuated to advance piston 32 within the interior of housing 14 to apply pressure to the cement during polymerization. The cement remains in this pressurized condition until it is ready to be applied, at which time nozzle valve 42 is opened by pushing inwardly on portion 44 and by deactuating valve 22 to decouple cylinder 18 from the supply of pressurized gas. When the cement is ready to be applied, trigger valve 22 is again actuated to drive piston 32 forwardly to force the cement through channel 46 and into a bone canal 99, as illustrated in FIG. 8, or into an acetabulum 110, as illustrated in FIG. 10.

Figure 7:
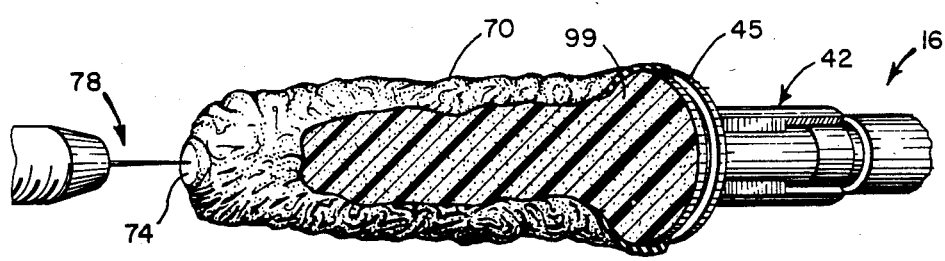
FIG. 7. is a partial cross-sectional view of the bladder and nozzle of FIG. 6.
Figure 6:
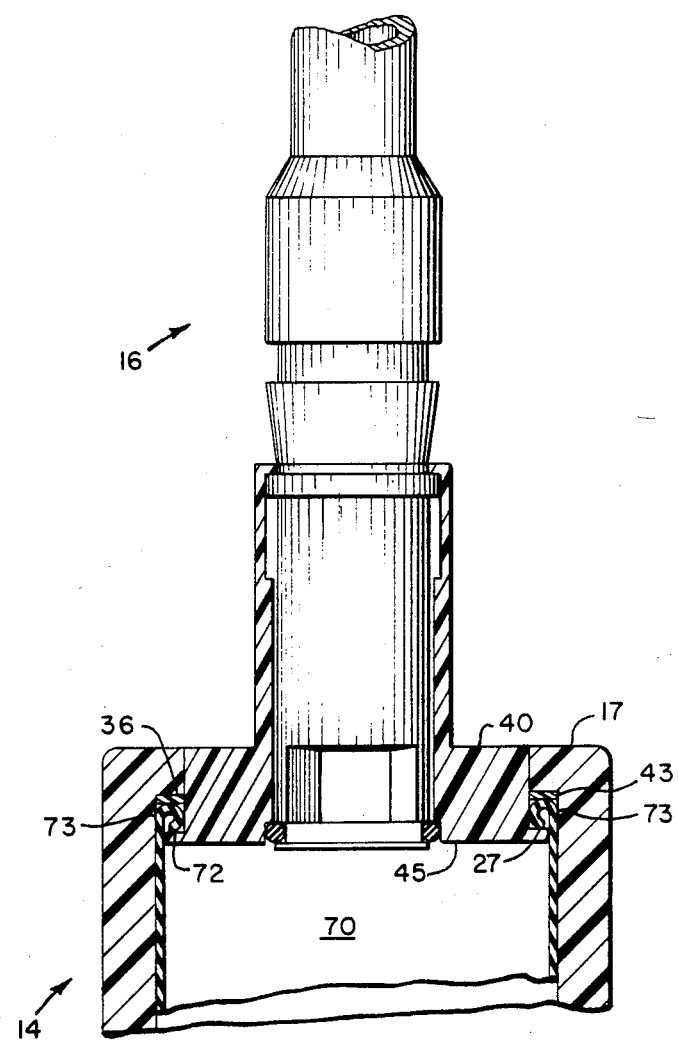
FIG. 6. is a cutaway cross-sectional view of one embodiment of the nozzle of this invention employing a bladder.

Another embodiment of this invention is illustrated in FIGS. 6 and 7 and like numbers are used for like parts, where possible. In this embodiment, nozzle 16 is formed separately of housing 14, and end wall 17 of housing 14 has an opening 40 through which nozzle 14 is inserted. Valve 42 has a radially extending flange 45 at one end which has an outside diameter generally equal to the inside diameter of opening 40. When inserted into housing 14, flange 45 resides in sealing engagement with opening 40 by the provision of laterally extending seals 43 which are forced tightly against inwardly facing shoulders 36 of opening 40 by pressure within housing 14. The powdered pre-polymerized cement is provided in a high vacuum in a sealed flexible bladder 70 which is secured to flange 45 of valve 42 prior to the coupling of nozzle 16 to housing 14, as illustrated in FIGS. 6 and 7. Bladder 70 is sealed, and secured to flange 45 by an elastic O-ring seal 72 which resides within a circumferential notch 73 formed in the outer surface of flange 45 below seal 43. Valve 42 is provided in a closed position to prevent contamination of the interior of bladder 70. A needle valve 74 is provided at the end of bladder 70 opposite of flange 45. In all other respects, housing 14 and nozzle 16 are identical to that shown in FIGS. 1-4.

Figure 9:
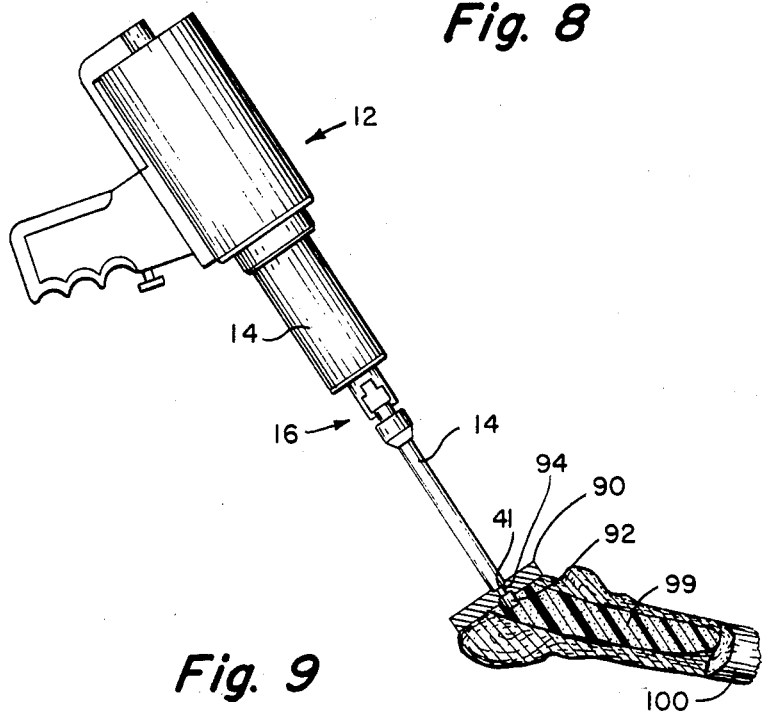
FIG. 9. is a pictorial representation of the use of the apparatus of this invention with a sealing gasket.

The method and operation of the apparatus of FIGS. 6 and 7 will now be described. The liquid monomer is injected into the interior of bladder 70 by a typical hypodermic needle 78 through needle valve 74, in a manner known to those skilled in the art. Valve 74 is such that after hypodermic needle 78 has been withdrawn, valve 74 seals itself to prevent air from entering bladder 70. The liquid monomer and powdered pre-polymerized cement can then be mixed by manually kneading bladder 70 to provide the desired level of mixing. In this manner, mixing of the monomer and polymer and polymerization all occur within a sealed environment, thus insuring that no ambient gases enter the cement. Thereafter, bladder 70 placed within housing 14, as shown in FIG. 6, and flange 45 of nozzle 16 is inserted into sealing engagement with opening 40 of housing 14. Housing 14 is then secured to gun 12, as previously described, and cylinder 18 is actuated to drive piston 32 against bladder 70 to compress bladder 70 to provide the desired pressure on the cement during polymerization. Once polymerization has been completed, valve 42 is opened as previously described and piston 32 is advanced to force cement from the interior of bladder 70 through ports 48 of valve 42 and through channel 46 into the canal 99 of a bone as shown in FIG. 8 or FIG. 9, or into an acetabulum 110, as illustrated in FIG. 10.

Figure 5:
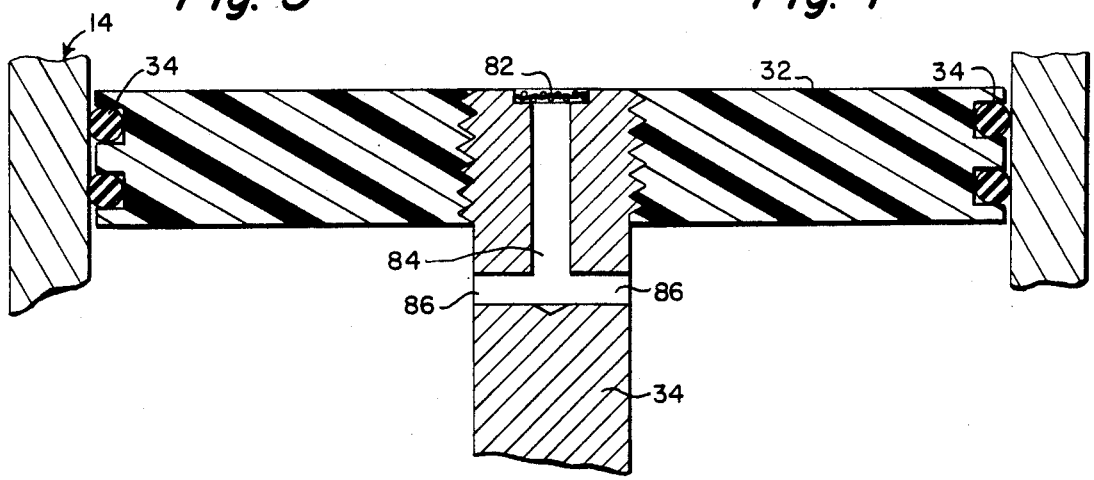
FIG. 5. is a cutaway cross-sectional view of the piston of this invention.

Another feature of this invention is illustrated in FIG. 5, and this feature can be used with either the embodiment of FIGS. 1-4 or that of FIGS. 6 and 7. Piston 32 is typically provided with a plurality of O-ring seals 34 around the outer radial perimeter thereof which ride in sliding engagement with the inner walls of housing 14 and which prevent cement from being forced between piston 32 and the inner walls of housing 14 as piston 32 is advanced. However, seals 34 also prevent the air residing within housing 14 between piston 32 and valve 42 from escaping, and such air could be injected into a bone cavity along with the cement, thus forming bubbles within the cement during delivery thereof. This is particularly true if bladder 70 is not employed and cement resides directly within housing 14. To overcome this problem, a filter or membrane 82 may be provided in the end of piston rod 34 adjacent piston 32 on the side thereof facing valve 42. Membrane 82 allows gases to pass therethrough, but not viscous cement. A channel 84 is provided in communication with filter 82 and extends generally along the central axis of piston rod 34 through the lateral extent of piston 32. Radially extending ports 86 are provided in outwardly facing surfaces of piston rod 34. Ports 86 communicate with channel 84 and allow gases therein to flow back into the interior of housing 14 on the side of piston 32 facing gun 12. In this manner, gases on the side of piston 32 facing valve 42 are allowed to escape to the other side facing gun 12 and are not injected into the cement. A vent hole is typically provided in housing 14 adjacent coupling 30 to allow such gases to escape from housing 14. Although piston rod 34 is shown as being threadably attached to piston 32, it may be attached thereto in any other suitable manner.

A further feature of this invention is the provision of a sealing gasket which will be described with reference to FIGS. 9 and 10. A gasket is attached to distal end 41 of portion 44, and the configuration of the gasket depends on the size and shape of the particular bone cavity into which the cement is to be injected. The gasket must seal the opening of the bone cavity to allow delivery of cement thereto under pressure, and thus has a cross-sectional size no less than the cross-sectional size of the bone cavity opening. One size gasket 90 is used for a canal 99 of a femur 100, as shown in FIG. 9, while a larger diameter gasket 112 is used for an acetabulum 110, as shown in FIG. 10. Gaskets 90 and 112 have a port 92 which registers with channel 46 to permit cement to flow from channel 46 through port 92 and into canal 99, as shown in FIG. 9, or into an acetabulum 110, as shown in FIG. 10. A shoulder 94 is provided within port 92 to engage the distal end 41 of portion 44 to arrest further movement thereof through port 92 and prevent it from being forced into the bone cavity. Gaskets 90 and 112 are typically formed of a thick, flexible material, such as silcone rubber, so that they can conform to the shape of the bone at the open mouth 97 of the bone canal 99 or at opening 114 of acetabulum 110 when pressed against it.

In the method of this embodiment, cement is first deposited into the bone cavity, starting at the bottom thereof and working toward the opening thereof, as illustrated for a femur 100 in FIG. 8. Once the cavity is filled with cement, gasket 90 or 112 is fixed to the distal end 41 of portion 44 so that distal end 41 is in registration with shoulder 94. Gun 12 is then manually held so that gasket 90 or 112 is applied respectively against open mouth 97 of bone canal 99 as shown in FIG. 9 or against opening 114 of acetabulum 110, as shown in FIG. 10. As manual, axially directed pressure is applied to nozzle 16, gasket 90 is forced against mouth 97 or gasket 112 is forced against opening 114 so that the surface of the gasket conforms to the shape of the surrounding bone so that gasket 90 or 112 seals its respective bone cavity. In this manner, cement within the cavity is prevented from escaping outwardly through mouth 97 or opening 114. Valve 22 is then actuated to drive piston 32 forwardly to urge cement into the cavity under pressure. This action applies pressure to the cement already residing within the cavity, thus forcing the existing cement into bone crevices and into the interstices in the interior surface of the cavity to provide a superior bond. The amount of pressure that can be applied to the cement is a function of the axial pressure applied by the holder of gun 12 and by the strength of gasket 90 or 112.

This invention provides apparatus that is far superior than any other existing device for applying cement to a bone cavity, particularly a medullary canal of a human femur or an acetabulum. Some of the polymerization occurs in a pressurized environment. As a result, the physical conditions under which the cement polymerizes are altered to produce a cement having a lower porosity and a greater strength. Also the gun may be used to apply pressure to the cement after its introduction into the canal to provide a better bond. As a result, a cement is formed which is much stronger and longer lasting than that produced by existing apparatus, and the bond between the bone and cement is far superior than that produced by known techniques. When bladder 70 is used, the steps of mixing, polymerization, delivery and pressure application are all performed by one piece of apparatus without the necessity of utilizing several different pieces of equipment, as in the prior art, and no ambient gases are introduced into the cement during polymerization.

In view of the above description, it is likely that modifications and improvements may occur to those skilled in the art within the scope of this invention. Thus, the above description is intended to be exemplary only, the scope of the invention being defined by the following claims and their equivalents.

What is claimed is:

1. Apparatus for application of cement to a bone cavity for implantation of a prosthetic device comprising:
   a generally rigid housing adapted to be sealed for pressurization thereof and for preventing a flow of gas therethrough, said housing holding a quantity of polymerizable cement prior to application to a bone cavity;
   means for applying pressure to a quantity of cement disposed within said housing during polymerization thereof to minimize the formation of gas bubbles in the cement;
   an elongated nozzle secured to said housing for delivery of cement to a bone cavity;
   a valve coupling said nozzle to said housing, said valve being in a normally closed position during application of pressure to a quantity of cement within said housing by said applying means, said applying means urging cement through said nozzle and said valve into a bone cavity only when said valve is in an open position;
   means for biasing said valve into said normally closed position, said valve being openable by a predetermined force to overcome said biasing means; and
   means for irreversibly locking said valve in said open position to prevent closure of said valve as cement is urged therethrough by said applying means.

2. Apparatus according to claim 1 further comprising:
   means securing said nozzle to said valve;
   means for removably securing said nozzle and said valve to said housing in sealed relation therewith;
   a sealed, flexible bladder having an interior chamber maintained at a high vacuum in communication with said valve and containing a powdered, pre-polymerized component of the cement; and
   means disposed on said bladder independently of said valve and said nozzle for introducing a liquid monomer into the interior of said bladder while maintaining the high vacuum within the interior chamber of said bladder, said liquid monomer being manually mixed with said pre-polymerized component by kneading of said bladder to produce polymerization thereof, said bladder being secured to said nozzle and said valve independently of said housing to allow replacement of said bladder, said valve and said nozzle in said housing.

3. Apparatus according to claim 1 wherein said applying means comprises:
   a pneumatically actuated cylinder;
   a piston disposed within said housing and driven by said cylinder; and
   filter means disposed in said piston for selectively allowing gases and not cement to pass therethrough.

4. Apparatus according to claim 1 further comprising gasket means disposed on an end of said nozzle spaced from said housing and adapted to be placed over the opening of a bone cavity for sealing thereof during application of cement into the bone cavity.

5. Apparatus according to claim 2 wherein said nozzle comprises a flange adapted to be inserted into an opening in a wall of said housing in sealing relation therewith, and wherein said bladder is sealingly secured to said nozzle flange.

6. Apparatus according to claim 2 wherein said valve means comprises a needle valve.

7. Apparatus according to claim 1 wherein said pressurizable housing is removably attached to said applying means.

8. Apparatus according to claim 3 further comprising:
   a piston rod connected to said piston within said housing and extending from said pneumatically actuated cylinder;
   a channel disposed within said piston rod in communication with said filter means; and
   means disposed in said housing in communication with said channel for venting gases within said channel to a point exterior of said housing.

9. A method for delivering a polymerizable cement to a bone cavity for implantation of a prosthesis comprising the steps of:
- mixing a liquid monomer with a powdered, pre-polymerized cement for polymerization thereof;
- placing the mixture of the monomer and pre-polymerized cement within a sealed, pressurizable housing having a normally closed valve;
- applying pressure to the mixture of the monomer and pre-polymerized cement in the sealed housing during polymerization thereof while preventing the escape of cement from the housing to minimize the formation of gas bubbles in the cement;
- opening the valve;
- locking the valve into an open position; and
- delivering the resulting polymerized cement to a bone cavity through the valve by continued application of pressure to the pressurizable housing.

10. A method according to claim 9 wherein said mixing step comprises the steps of:
- providing the powdered, pre-polymerized cement in a high vacuum in a sealed flexible bladder;
- injecting the liquid monomer into the sealed bladder; and
- manually kneading the sealed bladder to mix the monomer and pre-polymerized cement.

11. A method according to claim 9 further comprising the steps of applying a pressure seal to the opening of the bone cavity during said delivering step to force the cement into the crevices and interstices of the bone cavity.

12. Apparatus for application of cement to a bone cavity for implantation of a prosthetic device comprising:
- a manually operable, pneumatically actuated cylinder;
- a generally rigid housing being removably attachable to said cylidner, said housing being adapted to receive a quantity of cement prior to attachment thereof to said cylinder, the interior of said housing being sealed for preventing a flow of gas therethrough to allow pressurization thereof when said housing is secured to said cylinder;
- a piston disposed within said housing and driven by said pneumatically actuated cylinder for applying pressure to cement disposed within the interior of said sealed housing during polymerization of the cement to minimize the formation of gas bubbles in the cement;
- an elongated nozzle extending from said housing for application of cement to a bone cavity;
- a valve coupling said nozzle to said housing, said valve being in a normally closed position in which said nozzle is not in communication with the interior of said housing during application of pressure to cement disposed within the interior of said housing by said piston;
- means biasing said valve into said normally closed position, said valve being openable by the application of axial pressure to said nozzle toward said housing to overcome said biasing means; and
- means for irreversibly locking said valve in an open position in which said nozzle is in communication with the interior of said hosuing to allow cement to pass through said nozzle and into a bone cavity in response to pressure applied by said piston, said piston urging cement through said nozzle and said valve into a bone cavity only when said valve is in said open position.

* * * * *